(12) United States Patent
Chava et al.

(10) Patent No.: US 7,943,784 B2
(45) Date of Patent: May 17, 2011

(54) PROCESS FOR THE PREPARATION OF ALMOTRIPTAN

(75) Inventors: Satyanarayana Chava, Secunderabad (IN); Seeta Ramanjaneyulu Gorantla, Secunderabad (IN); Ramdas Chavakula, Secunderabad (IN); Babu Rao Konudula, Secunderabad (IN)

(73) Assignee: Matrix Laboratories Limited, Secunderabad (IN)

( * ) Notice: Subject to any disclaimer, the term of this patent is extended or adjusted under 35 U.S.C. 154(b) by 72 days.

(21) Appl. No.: 11/996,787

(22) PCT Filed: Jul. 21, 2006

(86) PCT No.: PCT/IN2006/000262
§ 371 (c)(1),
(2), (4) Date: May 21, 2008

(87) PCT Pub. No.: WO2007/013098
PCT Pub. Date: Feb. 1, 2007

(65) Prior Publication Data
US 2008/0234495 A1    Sep. 25, 2008

(30) Foreign Application Priority Data

Jul. 25, 2005   (IN) .............................. 993/CHE/2005

(51) Int. Cl.
*C07D 403/12* (2006.01)
(52) U.S. Cl. ...................................................... 548/467
(58) Field of Classification Search ................... 548/467
See application file for complete search history.

(56) References Cited

FOREIGN PATENT DOCUMENTS
ES   2084560 A1 *   5/1996

OTHER PUBLICATIONS

John A. Landgrebe, Theory and Practice in the Organic Laboratory, 4th edition, Chapter 6, p. 123-141, 1994.*

* cited by examiner

*Primary Examiner* — Yong Chu
(74) *Attorney, Agent, or Firm* — Workman Nydegger

(57) ABSTRACT

The present invention encompasses a method for the preparation of Almotriptan and its pharmaceutically acceptable salts comprises, i) Methylation of 3-[5-(1-Pyrrolidinyl sulfonyl methyl)1H-indol-yl]ethane amine ii) Treating crude Almotriptan with a hydroxy benzoic acid yields hydroxy benzoic acid addition salt of Almotriptan iii) Converting Almotriptan hydroxy benzoic acid addition salt to Almotriptan and iv) Salification of Almotriptan to its pharmaceutically acceptable salts.

3 Claims, No Drawings

PROCESS FOR THE PREPARATION OF ALMOTRIPTAN

RELATED APPLICATIONS

This application is a National Stage application filed under 35 U.S.C. §371 of PCT/IN2006/000262, filed Jul. 21, 2006, which claims the benefit of patent No. 993/CHE/2005 filed Jul. 25, 2005, all of which are herein incorporated by reference in their entirety.

The present invention relates to 1-[[[3-[2-(Dimethyl amino) ethyl]-1H-indol-5-yl]-methyl]sulfonyl]pyrrolidinone (Almotriptan) and its pharmaceutically acceptable salts, process for preparation thereof using the novel 1-[[[3-[2-(Dimethyl amino) ethyl]-1H-indol-5-yl]-methyl]sulfonyl]pyrrolidinone salicylate salt.

BACKGROUND OF THE INVENTION

1-[[[3-[2-(Dimethylamino)ethyl]-1H-indol 5-yl]-methyl] sulfonyl]pyrrolidinone (Almotriptan) has the formula as given below

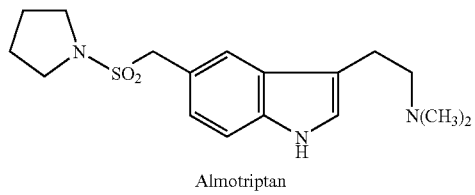

Almotriptan

Almotriptan is a selective $5-HT_{1B/1D}$ agonist used as a therapy for migraine headache, shows high and specific affinity for $5-HT_{1B/1D}$ receptors in cranial vessels, but poor affinity for $5-HT_{1A}$ and $5-HT_7$ receptors in peripheral arteries and therefore cause less side effects of hypertension by a central nervous system action and other side effects.

U.S. Pat. No. 5,565,447 discloses Almotriptan, its acid addition salts and the process for preparation. The disclosed process involves the decarboxylation of a carboxylic acid (Formula-I), in an inert organic solvent, in the presence of copper derivatives as a catalyst.

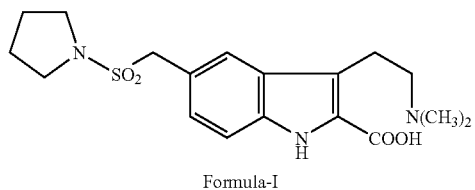

Formula-I

The disclosed process involves the column chromatographic purification with silica gel with methylene chloride: ethanol:ammonium hydroxide (60:8:1) as eluent. The U.S. Patent further discloses that the Almotriptan can be converted to acid addition salts with acids in appropriate solvents. Suitable acid addition salts disclosed are those derived from inorganic acids; for example hydrochloric acid and sulphuric acid.

Spanish Pat. No. 2,084,560 discloses the conversion of Almotriptan to its acid addition salts derived from organic, inorganic acids like malate, tartrate, succinate or hydrochloride. The procedure involved for preparation of DL-malate salt is by saltification with DL-malic acid in 96% ethanol.

Research Disclosure (1998) 412 discloses the synthetic pathway for preparation of Almotriptan by a sequence of reactions starting from the 4-substituted anilines (Scheme-1). The process for preparation of Almotriptan was also disclosed in Tetrahedron, 57 (2001) 1041-1048. The disclosed processes results the Almotriptan whose purity is not mentioned.

Scheme-1

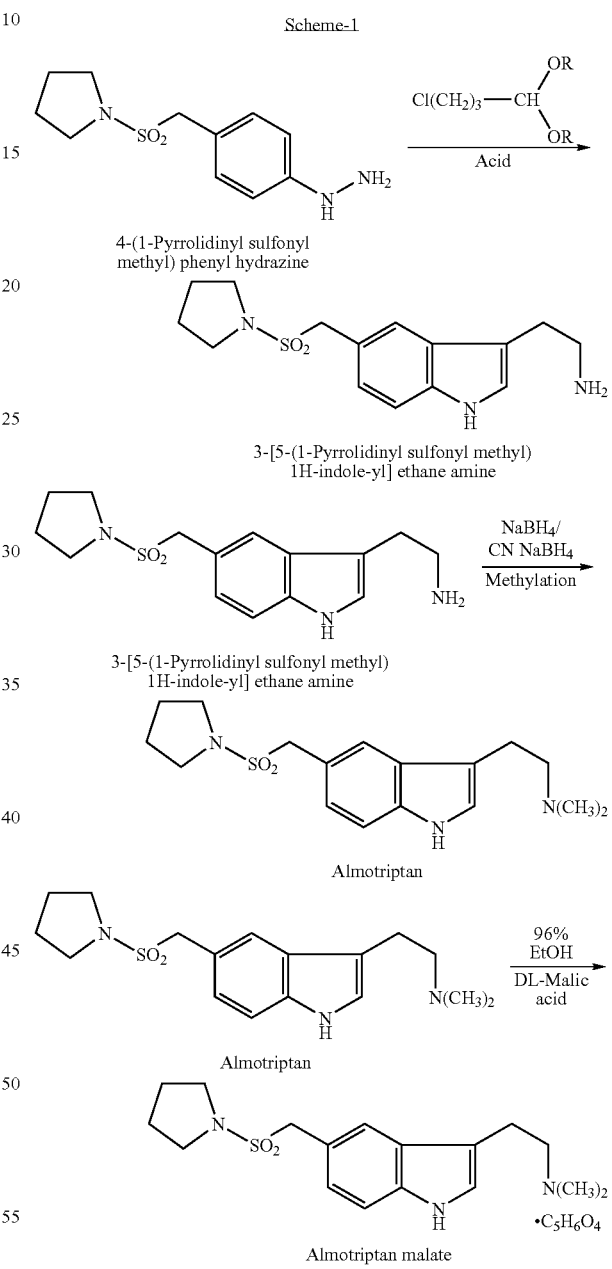

In the above-mentioned prior art processes Almotriptan malate with pharmaceutically acceptable purity is achieved by the saltification of pure Almotriptan with malic acid.

It is observed that Almotriptan pharmaceutically acceptable salts being prepared by Almotriptan with less purity is not meeting with the pharmaceutically acceptable quality. There is therefore an unfulfilled need to provide industrially feasible process for the preparation of pharmaceutically acceptable salts of Almotriptan from impure Almotriptan without column chromatography purification as described in the prior art.

To overcome the problem inventors have tried to prepare Almotriptan pharmaceutically acceptable salts through Almotriptan acid addition salts from Almotriptan irrespective of its purity.

It is surprisingly found by the inventors that when the impure Almotriptan is reacted with hydroxy benzoic acids such as 2-Hydroxy benzoic; acid (Salicylic acid) and 4-hydroxy benzoic acid, it selectively forms the corresponding acid addition salt, leaving behind the other related substances and impurities which are otherwise difficult to remove by the conventional methods. The hydroxy benzoic acid salts of Almotriptan are further converted to Almotriptan pharmaceutically acceptable salts with acceptable purity.

SUMMARY OF THE INVENTION

The main object of the present invention is to provide an improved process for the preparation of Almotriptan and/or its pharmaceutically acceptable salts.

Another object of the invention is to provide a process for preparation of Almotriptan and/or its pharmaceutically acceptable salts using hydroxybenzoic acid salts of Almotriptan.

Accordingly in the present invention Almotriptan and its pharmaceutically acceptable salts are prepared by i) converting impure Almotriptan to its hydroxybenzoic acid salts ii) neutralizing hydroxybenzoic acid salts and isolating Almotriptan and iii) converting Almotriptan to its pharmaceutically acceptable salts

DETAILED DESCRIPTION OF THE INVENTION

Thus in accordance with the present invention preparation of Almotriptan, its pharmaceutically acceptable salts comprise the following steps;
  i. Methylation of 3-[5-(1-Pyrrolidinyl sulfonyl methyl) 1H-indol-yl]ethane amine with formaldehyde and sodium borohydride yields crude Almotriptan
  ii. Treating crude Almotriptan with a hydroxy benzoic acid yields hydroxy benzoic acid addition salt of Almotriptan.
  iii. Converting Almotriptan hydroxy benzoic acid addition salt to Almotriptan
  iv. Saltification of Almotriptan to its pharmaceutically acceptable salts In a specific embodiment, the present invention provides a process for the preparation of Almotriptan and its pharmaceutically acceptable salts, which involves,
  i. Dissolution of 3-[5-(1-Pyrrolidinyl sulfonyl methyl) 1H-indol-yl]ethane amine in methanol,
  ii. Simultaneous slow addition of formaldehyde solution in methanol followed by aqueous sodium borohydride solution at temperature of 0 to 15° C. preferably at 5 to 10° C., over a period of 1 hr to 6 hrs preferably over 2 to 4 hrs
  iii. Acidification of the reaction mass with hydrochloric acid
  iv. Neutralizing with alkali carbonates, alkali bicarbonates such as sodium carbonate, sodium bicarbonate, potassium carbonate, potassium bicarbonate, preferably with sodium carbonate,
  v. Removing methanol below 60° C. under vacuum,
  vi. Washing the reaction mass with ethyl acetate,
  vii. Adjusting the pH to 9.0 to 12.0 with alkali carbonate preferably potassium carbonate,
  viii. Separating the layers and the organic layer is concentrated under reduced pressure to get the crude residue of Almotriptan Further reacting the resultant crude residue of Almotriptan with hydroxy benzoic acid by
  i. Dissolving the residue in a short chain alcohol such as methanol, ethanol, propanol or mixture thereof,
  ii. Adding hydroxy benzoic acid directly or as a solution in short chain alcohol,
  iii. Maintaining the reaction mixture at 35° C. to reflux temperature of the solvent for about 30 min to 2 hrs
  iv. Cooling the reaction mixture to 10 to 35° C.
  v. Isolating the precipitated product and dying the product at 40 to 90° C., preferably at 50 to 75° C., affords the pure Almotriptan as an acid addition salt of hydroxy benzoic acid.

The prepared Almotriptan hydroxy benzoic acid addition salts (both 2-hydroxy benzoic acid and 4-hydroxy benzoic acid) are novel, identified and characterized by chemical analysis, IR, NMR & Mass spectral data. Almotriptan hydroxy benzoic acid addition salt is further converted to Almotriptan by
  i. Neutralizing Almotriptan hydroxy benzoic acid with a base such as organic amines, alkali hydroxides, alkali carbonates, alkali bicarbonates and ammonia, in a mixture of water and water immiscible solvent
  ii. Separating the layers,
  iii. Washing the organic layer with water,
  iv. Concentrating the organic layer under vacuum affords Almotriptan The obtained Almotriptan is further converted to Pharmaceutically acceptable salts of Almotriptan by
  i. Dissolving Almotriptan in an alcohol such as methanol, ethanol and propanol
  ii. Treating with activated carbon,
  iii. Saltification with a pharmaceutically acceptable organic acid, such as maleic acid, DL-malic acid and Tartaric acid,
  iv. Isolating the precipitated salt by conventional methods,
  v. Drying the product at 40° C. to 100° C., preferably at 50 to 80° C. affords the corresponding Almotriptan acid addition salts in pure form.

The required 3-[5-(1-Pyrrolidinyl sulfonyl methyl) 1H-indol-yl]ethane amine can be prepared by the prior art processes.

The invention is further illustrated with a few non-limiting examples

EXAMPLE-1

Preparation Almotriptan Malate

Prepared from Almotriptan Crude

Almotriptan crude (10 gms, purity 87.39%) is dissolved in Ethanol (50 ml) at room temperature. Reaction mass is stirred for 15 min for the complete dissolution. Malic Acid solution (4.6 gms in 21 ml Ethanol) is added to the above solution over 30 min at room temperature. Reaction mass temperature is raised to reflux and maintained for about 1 hr at that temperature. Slowly cooled the reaction mass to room temperature and maintained for about 2.0 hrs. The precipitated material is filtered and washed with 15 ml of Ethanol.

Dried the material at 70-75° C. under vacuum till constant weight.
Dry Weight: 9.2 gms: Purity 97.34% (by HPLC)

EXAMPLE-2

Preparation of Almotriptan Oxalate

Almotriptan crude (10 gms, purity 92.5%) is dissolved in Ethanol (60 ml) at room temperature. Reaction mass is stirred for 15 min for the complete dissolution. Oxalic Acid solution (4.0 gms in 15 ml Ethanol) is added to the above solution over 30 min at room temperature. Reaction mass temperature is raised to reflux and maintained for about 6 hrs. Slowly cooled the reaction mass to 0° C. and maintained for about 1 hr at 0±3° C. The precipitated material is filtered and washed with 15 ml of Ethanol.
Dried the product at 70-75° C. under vacuum till constant weight.
Dry Weight: 5.0 gms: Purity 93.05% (by HPLC)

EXAMPLE-3

Preparation Almotriptan Malate from Almotriptan Oxalate

Almotriptan oxalate (10 gms) is suspended in dissolved in ethyl acetate (250 ml). Aqueous ammonia solution (100 ml) is added over a period of 30 min. The mass is maintained for 30 min and allowed to settle. Layers are separated and the aqueous layer is extracted with ethyl acetate (100 m). Combined the organic layer and washed with water (100 ml). The organic layer is dried over sodium sulphate and distilled off under vacuum at temperature below 50° C. Methanol (40 ml) is added to the mass, stirred at room temp for clear solution. DL-Malic acid solution (8.6 gms in 20 ml methanol) is added slowly over 30 min. Reaction mass temperature is raised to reflux and maintained for 1 hr. Cooled the reaction mass to room temperature and maintained at 25-35° C. for 3 hrs. Precipitated product is filtered and washed with methanol (20 ml). The product is dried at temperature of 70-75° C. till constant weight.
Dry weight of Almotriptan malate: 4.4 gms Purity: 94.08% (by HPLC)

EXAMPLE-4

Preparation of Almotriptan 2-Hydroxy Benzoate

Salicylate

Almotriptan crude (10 gms, purity 87.39%) is dissolved in Ethanol (50 ml) at room temperature. Reaction mass is stirred for 15 min for the complete dissolution. Salicylic acid solution (5.3 gms in 20 ml Ethanol) is added to the above solution over 30 min at room temperature. Reaction mass temperature is raised to reflux and maintained for about 1 hr at that temperature. Slowly cooled the reaction mass to room temperature and maintained for about 2.0 hrs. The precipitated material is filtered and washed with 20 ml of Ethanol.
Dried the material at 70-75° C. under vacuum till constant weight.
Dry Weight: 11.5 gms Purity 99.22% (by HPLC)

EXAMPLE-5

Preparation Almotriptan Malate from Almotriptan 2-Hydroxy Benzoate Salicylate

Almotriptan salicylate (10 gms) is suspended in a mixture of water (100 ml) and ethyl acetate (100 ml) at a temperature of 25-30° C. Aqueous ammonia solution (25 ml) is added to the suspension over a period of 30 min. The mass is maintained for 30 min and allowed to settle. Layers are separated and the aqueous layer is extracted with ethyl acetate (2×50 ml). Combined the organic layer and washed with water (2×50 ml) and ethyl acetate is distilled off under vacuum at temperature below 50° C. The crude product is dissolved in Methanol (20 ml), stirred at room temp for clear solution. The organic layer is treated with activated charcoal (1 gms) for 30 min at 25-30° C. and filtered the mass through hyflow bed. The hyflow bed is washed methanol (5 ml). To the clear filtrate Malic acid solution (3.2 gms in 15 ml) is added slowly over 30 min and maintained the mass at reflux for 1 hr. Slowly cooled the reaction mass to room temperature and maintained at 25-35° C. for 3 hrs. Precipitated product is filtered and washed with chilled methanol (60 ml). The product is dried at temperature of 70-75° C. till constant weight.
Dry weight of Almotriptan malate is 9.0 gms Purity: 99.81% (by HPLC)

We claim:
1. A process for the preparation of purified Almotriptan malate, comprising the steps of:
   i. treating crude Almotriptan with 2-hydroxy benzoic acid to yield a 2-hydroxy benzoic acid addition salt of Almotriptan;
   ii. converting the Almotriptan 2-hydroxy benzoic acid addition salt to Almotriptan in presence of a base; and
   iii. reacting the Almotriptan yielded in step ii) with malic acid in alcoholic solvent to provide a malate salt of Almotriptan.
2. The process according to claim 1, wherein the base in step ii) is ammonia.
3. The process according to claim 1, wherein the alcoholic solvent in step iii) is methanol.

* * * * *